(12) United States Patent
Thomson et al.

(10) Patent No.: US 11,696,676 B2
(45) Date of Patent: Jul. 11, 2023

(54) OPTICAL SYSTEM AND METHOD

(71) Applicant: The University Court of the University of Edinburgh, Edinburgh (GB)

(72) Inventors: Robert R Thomson, Edinburgh (GB); Debaditya Choudhury, Edinburgh (GB); Tim Birks, Bath (GB)

(73) Assignees: THE UNIVERSITY OF BATH, Bath (GB); HERIOT-WATT UNIVERSITY, Edinburgh (GB)

( * ) Notice: Subject to any disclaimer, the term of this patent is extended or adjusted under 35 U.S.C. 154(b) by 0 days.

(21) Appl. No.: 16/610,802

(22) PCT Filed: May 4, 2018

(86) PCT No.: PCT/GB2018/051214
§ 371 (c)(1),
(2) Date: Nov. 4, 2019

(87) PCT Pub. No.: WO2018/203088
PCT Pub. Date: Nov. 8, 2018

(65) Prior Publication Data
US 2020/0069165 A1    Mar. 5, 2020

(30) Foreign Application Priority Data

May 5, 2017   (GB) ..................... 1707239

(51) Int. Cl.
*A61B 1/00* (2006.01)
*A61B 1/06* (2006.01)
(Continued)

(52) U.S. Cl.
CPC ...... *A61B 1/00165* (2013.01); *A61B 1/00009* (2013.01); *A61B 1/00057* (2013.01);
(Continued)

(58) Field of Classification Search
CPC ... A61B 1/07; A61B 1/00057; A61B 1/00126; A61B 1/04; A61B 1/063; A61B 1/0638;
(Continued)

(56) References Cited

U.S. PATENT DOCUMENTS

| 5,956,447 A * | 9/1999 | Zel'Dovich | G02B 6/02 385/27 |
| 2002/0062082 A1* | 5/2002 | Ohara | A61B 1/00082 600/462 |

(Continued)

FOREIGN PATENT DOCUMENTS

| EP | 2953215 | 12/2015 |
| FR | 2852394 | 9/2004 |

(Continued)

OTHER PUBLICATIONS

Baris I. Erkmen and Jeffrey H. Shapiro, Ghost imaging: from quantum to classical to computational, 2010, Optical Society of America, p. 405 (Year: 2010).*

(Continued)

*Primary Examiner* — Ryan N Henderson
*Assistant Examiner* — Sung Ham
(74) *Attorney, Agent, or Firm* — Snell & Wilmer L.L.P.

(57) ABSTRACT

A system comprises a waveguide apparatus comprising a plurality of input waveguides, a multimode waveguide, and a guided-wave transition coupling the plurality of input waveguides to the multimode waveguide. The system further comprises at least one light source configured to excite in turn each of a plurality of the input waveguides, or each of a plurality of combinations of the input waveguides, thereby generating a plurality of different light patterns in turn at an output of the waveguide apparatus. The waveguide apparatus is configured to direct each of the plurality of different light patterns to a target region. The system further (Continued)

comprises at least one detector configured to detect light transmitted, reflected or emitted from the target region in response to each of the different light patterns, and to output signals representing the detected light.

24 Claims, 8 Drawing Sheets

(51) Int. Cl.

| | |
|---|---|
| *A61B 1/07* | (2006.01) |
| *F21V 8/00* | (2006.01) |
| *G02B 6/02* | (2006.01) |
| *G02B 6/024* | (2006.01) |

(52) U.S. Cl.
CPC ............ *A61B 1/00126* (2013.01); *A61B 1/06* (2013.01); *A61B 1/063* (2013.01); *A61B 1/0638* (2013.01); *A61B 1/07* (2013.01); *G02B 6/0008* (2013.01); *G02B 6/024* (2013.01); *G02B 6/02042* (2013.01)

(58) Field of Classification Search
CPC ... A61B 1/06; A61B 1/00165; A61B 1/00009; A61B 1/0017; A61B 1/00013; G02B 6/0008; G02B 6/02042; G02B 6/024; G02B 6/14; G02B 6/2804; G02B 6/2808
USPC .......................................................... 600/109
See application file for complete search history.

(56) References Cited

U.S. PATENT DOCUMENTS

| | | | |
|---|---|---|---|
| 2005/0018185 A1 | 1/2005 | Genet et al. | |
| 2005/0078924 A1 | 4/2005 | Viellerobe et al. | |
| 2005/0157981 A1 | 7/2005 | Berier et al. | |
| 2005/0190372 A1* | 9/2005 | Dogariu | G01N 21/49 |
| | | | 356/479 |
| 2005/0207668 A1 | 9/2005 | Perchant et al. | |
| 2005/0242298 A1 | 11/2005 | Genet et al. | |
| 2006/0056017 A1 | 3/2006 | Berier et al. | |
| 2006/0079762 A1* | 4/2006 | Norris | A61B 1/2676 |
| | | | 600/427 |
| 2006/0100490 A1* | 5/2006 | Wang | A61B 5/441 |
| | | | 600/310 |
| 2006/0256194 A1 | 11/2006 | Viellerobe et al. | |
| 2007/0177104 A1 | 8/2007 | Lacombe et al. | |
| 2007/0273930 A1 | 11/2007 | Berier et al. | |
| 2007/0290145 A1 | 12/2007 | Viellerobe et al. | |
| 2008/0029711 A1 | 2/2008 | Viellerobe et al. | |
| 2008/0045848 A1 | 2/2008 | Lacombe et al. | |
| 2008/0225231 A1 | 9/2008 | Lacomb et al. | |
| 2008/0231807 A1 | 9/2008 | Lacombe et al. | |
| 2008/0315119 A1* | 12/2008 | Blackmore | G01N 21/645 |
| | | | 702/19 |
| 2009/0021739 A1* | 1/2009 | Tsujita | H04N 5/2256 |
| | | | 356/407 |
| 2009/0023999 A1 | 1/2009 | Mathieu et al. | |
| 2009/0041314 A1 | 2/2009 | Vercauteren et al. | |
| 2009/0097806 A1 | 4/2009 | Viellerobe et al. | |
| 2009/0240143 A1 | 9/2009 | Osdoit et al. | |
| 2010/0168610 A1 | 7/2010 | Lacombe et al. | |
| 2010/0234686 A1 | 9/2010 | Lacombe et al. | |
| 2010/0296178 A1 | 11/2010 | Genet et al. | |
| 2010/0309477 A1* | 12/2010 | Yun | G01J 3/021 |
| | | | 356/497 |
| 2011/0015529 A1 | 1/2011 | Abrat et al. | |
| 2011/0133101 A1 | 6/2011 | Viellerobe et al. | |
| 2011/0254980 A1 | 10/2011 | Perchant et al. | |
| 2011/0274325 A1 | 11/2011 | Vercauteren et al. | |
| 2011/0317963 A1 | 12/2011 | Rocher et al. | |
| 2012/0035484 A1 | 2/2012 | Thiberville et al. | |
| 2012/0123236 A1 | 5/2012 | Boularot et al. | |
| 2012/0184842 A1 | 7/2012 | Boularot et al. | |
| 2013/0237976 A1* | 9/2013 | Temelkuran | G02B 6/02385 |
| | | | 606/16 |
| 2014/0104619 A1 | 4/2014 | Nebosis | |
| 2014/0117207 A1 | 5/2014 | Savoire et al. | |
| 2014/0207150 A1 | 7/2014 | Rosa et al. | |
| 2014/0209798 A1 | 7/2014 | Woodward et al. | |
| 2015/0057499 A1 | 2/2015 | Erden et al. | |
| 2015/0086157 A1 | 3/2015 | Fontaine et al. | |
| 2015/0104394 A1 | 4/2015 | Abbaci et al. | |
| 2016/0253801 A1 | 9/2016 | Linard et al. | |
| 2017/0299900 A1* | 10/2017 | Montoya | G02F 1/0121 |
| 2017/0343791 A1* | 11/2017 | Swanson | A61B 1/00165 |
| 2021/0018744 A1* | 1/2021 | Rigneault | G02B 23/2423 |

FOREIGN PATENT DOCUMENTS

| | | |
|---|---|---|
| FR | 2865369 | 7/2005 |
| JP | H5256754 | 10/1993 |
| JP | H663048 | 3/1994 |
| JP | 2011232674 A * | 11/2011 |
| JP | 201421127 | 2/2014 |
| JP | 201555706 | 3/2015 |
| JP | 2016202360 | 12/2016 |
| WO | 2015153982 | 10/2015 |
| WO | 2016027797 | 2/2016 |
| WO | 2017073737 | 5/2017 |
| WO | 20171745964 | 10/2017 |

OTHER PUBLICATIONS

Tomas Cizmarand Kishan Dholakia, Exploiting multimode waveguides for pure fibre-based imaging, 2012, Nature Communications, pp. 1-9 (Year: 2012).*
Exploitin multimode waveguides for pire fibre-based imagin, T Cizmar et al., Nature communications, 3:1027, pp. 1-9; Aug. 5, 2012.
International Search Report and Written Opinion dated Aug. 11, 2018 in PCT/GB2018/051214.
IPO; International Preliminary Report on Patentability dated Nov. 5, 2019 in Application No. PCT/GB2018/051214.
Čižmár, T. & Dholakia, K. Exploiting multimode waveguides for pure fibre-based imaging. Nat. Comms. 3, 1027 (2012).
Y. Choi et al, "Scanner-Free and Wide-Field Endoscopic Imaging by Using a Single Multimode Optical Fiber," Phys. Rev. Lett. 109, 203901 (2012).
Mahalati, R. N., Askarov, D., Wilde, J. P. & Kahn, J. M. Adaptive control of input field to achieve desired output intensity profile in multimode fiber with random mode coupling. Optics Express 20, 14321-14337 (2012).
Mahalati, R. N., Gu, R. Y. & Kahn, J. M. Resolution limits for imaging through multi-mode fiber. Optics Express 21, 1656-1668 (2013).
Birks, T. A., Gris-Sánchez, I., Yerolatsitis, S., Leon-Saval, S. G. & Thomson, R. R. The photonic lantern. Adv. Opt. Photon. 7, 107 (2015).
Baoqing Sun, Stephen S. Welsh, Matthew P. Edgar, Jeffrey H. Shapiro, and Miles J. Padgett, "Normalized ghost imaging," Optics Express 20, 16892-16901 (2012).
Shin, J., Bosworth, B. T. & Foster, M. A. Single-pixel imaging using compressed sensing and wavelength-dependent scattering. Optics Letters 41, 886 (2016).
Shin, J., Bosworth, B. T. & Foster, M. A. Compressive fluorescence imaging using a multi-core fiber and spatially dependent scattering, Optics Letters 42 (1), 109-112 (2017).
Rodrigo A. Vicencio et al, Observation of Localized States in Lieb Photonic Lattices, PRL 114, 245503 (2015).
Kim, Y., Knight, J., Warren, S., Neil, M., Paterson, C., Stone, J., Dunsby, C. and French, P., 2016. Adaptive multiphoton endomicroscope incorporating a polarization-maintaining multicore optical fiber. IEEE Journal of Selected Topics in Quantum Electronics, 22 (3), 6800708.

(56) References Cited

OTHER PUBLICATIONS

Harikumar K. Chandrasekharan et al, Multiplexed single-mode wavelength-to-time mapping of multimode light, Nature Communications | 8:14080 | DOI: 10.1038/ ncomms14080.

S. Yerolatsitis, K. Harrington, R. R. Thomson, and T. A. Birks, "Mode-selective Photonic Lanterns from Multicore Fibres," in Optical Fiber Communication Conference, OSA Technical Digest (online) (Optical Society of America, 2017), paper Tu3J.6.

D. Choudhury, A. Rodenas, L. Paterson, D. Jaque, and A. K. Kar, "3D Microfabrication in YAG Crystals by Direct Laser Writing and Chemical Etching," in 2013 Conference on Lasers and Electro-Optics Pacific Rim, (Optical Society of America, 2013), paper WPE_14.

Ming-Jie Sun et al, Single-pixel three-dimensional imaging with time-based depth resolution, Nat Commun. Jul. 5, 2016;7:12010. doi: 10.1038/ncomms12010.

China National Intellectual Property Administration, Chinese Office Action dated Dec. 3, 2021 in Application No. 201880041799.5.

Montoya, et al., "Photonic Lantern Adaptive Spatial Mode Control in LMA Fiber Amplifiers", Optics Express, Feb. 9, 2016, vol. 24, p. 3405-3413, DOI: 10.1364/OE.24.003405.

Japanese Patent Office, Japanese Office Action dated Oct. 11, 2022 in Application No. 2019-559697.

Korean Patent Office, Korean Office Action dated Dec. 28, 2022 in Application No. 10-2019-7033428.

Proteus, "Lighting up the Lung, Detecting Disease" Proteus overview document, 2015, www.proteus.ac.uk, The University of Edinburgh, pp. 1-14.

* cited by examiner

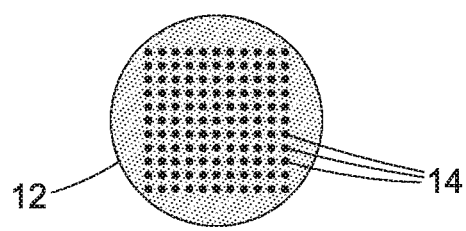
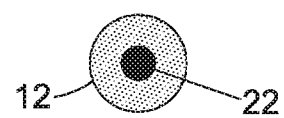
Fig. 2a  Fig. 2b
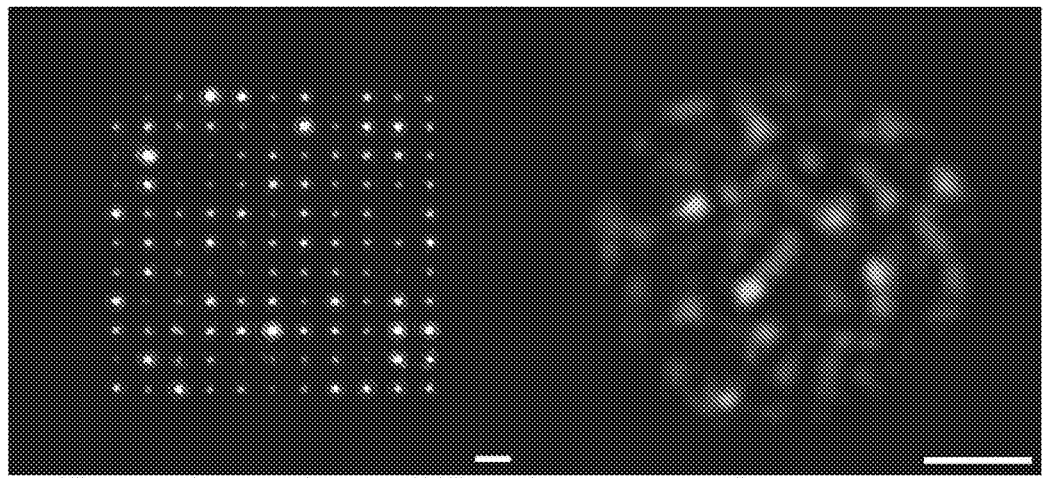
Fig. 3a  Fig. 3b (a) (b) (c)

OPTICAL SYSTEM AND METHOD

CROSS-REFERENCE TO RELATED APPLICATIONS

This application is a U.S. national phase filing of PCT/GB2018/051214 (the "214 application") under 35 U.S.C. § 371, that was filed on May 4, 2018 and titled, "Optical System and Method." The '214 application claims priority from the Great Britain Application No. 1707239.8 filed May 5, 2017 and titled, "Optical System and Method." Both of the aforementioned applications are incorporated herein by reference in their entireties for all purposes.

FIELD

The present invention relates to an optical system and method, for example a system and method in which an optical fibre apparatus is used to perform in vivo endoscopic imaging.

BACKGROUND

In the field of in vivo biomedical imaging, optical fibres may provide an attractive minimally invasive tool for obtaining images of tissue and microenvironments deep within hard to reach regions of the human anatomy.

However, a fundamental challenge associated with image transmission using optical fibres may be that multimode fibres act to scramble the phase and amplitude information that may typically be required to transmit a clear image from one end of a fibre to the other. Therefore, imaging using a multimode fibre may be challenging.

One approach to attempt to bypass this issue is to use a coherent fibre bundle. A coherent fibre bundle may be a fibre that contains many individual guiding cores that are minimally coupled over the length of fibre, and that support only one or a few modes at a desired wavelength. By using these cores to transmit light to and from an object of interest, it may be possible to sample the object in real time, which may make in situ application possible.

When using coherent fibre bundles, the resolution of the obtained image may be directly determined and limited by the size and spacing of the individual cores forming the bundle.

Endoscopic imaging systems using coherent fibre bundles are now commercially available and may provide the only commercially available means to achieve in vivo in situ single fibre imaging. However, such coherent fibre bundles may be difficult to engineer and may only work for a relatively narrow spectral bandwidth. Coherent fibre bundles are carefully designed in terms of the core size, spacing and number, which may make even short lengths of these coherent fibre bundles expensive. Moreover, it appears unlikely that the resolution limits already achieved by fibre bundles may be improved much further.

Fueled by the desire for increased information capacity, resolution enhancement and miniaturisation, the use of single-core multimode fibres for imaging has been the focus of much research in recent years. In particular, a number of methods have been investigated that rely on acquiring a priori knowledge of the fibre's transmission matrix, which may then be corrected for by using spatial light modulators to undo the fibre scrambling. Other methods rely on pre-calibrating the patterns generated at the fibre output as a function of the input. Post-processing algorithms may then be used to reconstruct the object by measuring the amount of light returned to the proximal end for different input patterns. Regardless of the method, many current techniques using multimode fibres require some form of pre-calibration of the system.

In an in vivo system, there may be no access to the distal end of the fibre, which may prevent use of methods that depend on access to the distal end in order to perform real-time calibration.

The transmission matrix of a length of multimode fibre is not robust and is easily altered by even a slight movement of the fibre. The transmission matrix may change randomly as the fibre moves or bends within the body. It may not be possible to compensate for random changes in the transmission matrix as the fibre moves and bends within the body without having access to the distal end. The transmission matrix may also be wavelength dependent.

SUMMARY

In a first aspect of the system, there is provided a system comprising a waveguide apparatus comprising a plurality of input waveguides, a multimode waveguide, and a guided-wave transition coupling the plurality of input waveguides to the multimode waveguide; at least one light source configured to excite in turn each of the input waveguides, or each of a plurality of combinations of the input waveguides, thereby generating a plurality of different light patterns in turn at an output of the waveguide apparatus, wherein the waveguide apparatus is configured to direct each of the plurality of different light patterns to a target region; and at least one detector configured to detect light transmitted, reflected or emitted from the target region in response to each of the different light patterns, and to output signals representing the detected light.

The system may further comprise a processing resource configured to process the signals from the at least one detector to obtain information about the target region.

The system may further comprise a processing resource configured to process the signals from the at least one detector to obtain an image of the target region.

Using a guided-wave transition to couple a plurality of input waveguides to a multimode waveguide may provide a straightforward, repeatable method for obtaining a plurality of light patterns at the output of the multimode waveguide. The light patterns that are produced may be stable with regard to movement of the waveguide apparatus. The plurality of light patterns may then be used to perform imaging of the target region.

By directing a plurality of light patterns onto the target region and detecting light from the target region in response to each of the light patterns, an image of the target region may be formed that has a high resolution. In some circumstance, the image may comprise a super resolution image.

The imaging may have a high fill factor. The multimode waveguide may have a high numerical aperture. Light may be directed to and/or detected from all or most of the target region, instead of being sampled from small parts of the target region. The system may provide efficient delivery of light from the at least one light source to the target region and/or efficient collection of light from the target regions. The system may be capable of broadband operation.

The guided-wave transition may be a region of the waveguide apparatus in which waves travelling down the input waveguides are guided into the multimode waveguide. A mode propagating in an input waveguide may evolve in the guided-wave transition such that a plurality of modes are generated in the multimode waveguide. In operation, one or more modes propagating in the input waveguides may evolve into modes propagating in the multimode waveguide in a substantially continuous fashion. Modes propagating from the distal end of the waveguide apparatus in the multimode waveguide may evolve in the guided-wave transition into modes propagating in the input waveguides. Light propagating in a single mode in an input waveguide may no longer be single mode after entering the guided-wave transition, and may be multimode on exiting the guided-wave transition. The guided-wave transition may provide an interface between the plurality of input waveguides (which may each be single mode or few-mode) and the multimode waveguide. In the guided-wave transition, the waveguide may change smoothly from one type (single- or few-mode) to another type (multimode). Light may be coupled between the input waveguides and multimode waveguides with low loss.

The waveguide apparatus may comprise an optical fibre. Each of the input waveguides may comprise a respective core of a multi-core section of the optical fibre. The multimode waveguide may comprise a multimode section of the optical fibre.

The guided-wave transition may comprise a substantially continuous transition from the cores of the multi-core section of the optical fibre to the multimode section of the optical fibre. The guided-wave transition may be a section of the optical fibre that couples the cores of the multi-core section of the optical fibre to the multi-mode section of the optical fibre. The guided-wave transition may smoothly guide modes propagating in the multi-core section into the multimode section (or vice versa). The guided-wave transition may comprise a photonic lantern transition. A material from which the guided-wave transition is formed may comprise at least one of a glass (for example, silicate or chalcogenide), a crystalline material, a polycrystalline material, a ceramic material.

The optical fibre may be formed by tapering one end of a multicore fibre to form the guided-wave transition.

The optical fibre may be flexible. The optical fibre may be capable of being inserted into a human or animal body. The optical fibre may be suitable for use in vivo. The optical fibre may comprise silica. The optical fibre may have a diameter of 2 mm or less. The optical fibre may comprise a polymer.

The system may be used to obtain images of tissue within the human or animal body. For example, the system may be used to image the distal lung, the gastrointestinal tract, the urinary tract, or the brain. The system may be used to perform minimally invasive imaging.

The at least one light source may be configured to excite the input waveguides with excitation light that is such as to cause fluorescence in the target region. The at least one detector may be configured to detect fluorescent light emitted by the target region in response to the excitation light.

The at least one detector may be coupled to a proximal end of the waveguide apparatus. The target region may be positioned at or near a distal end of the waveguide apparatus. Light reflected or emitted from the target region in response to each of the different light patterns may be received by the at least one detector through some or all of the input waveguides.

The system may comprise or form part of an endoscopic apparatus. The endoscopic apparatus may comprise an endoscopic imaging apparatus.

Each of the input waveguides may be a single mode waveguide. Each of the input waveguides may be single mode at a frequency of light that is used to excite the input waveguides.

Each of the input waveguides may be a few-mode waveguide. Each of the input waveguides may be configured to support a plurality of spatial modes. Each of the input waveguides may be configured to support no more than 40 modes, optionally no more than 10 modes, further optionally no more than 6 modes, further optionally no more than 3 modes at a frequency of light that is used to excite the input waveguides. Each of the input waveguides may be configured to support 10 modes. Each of the input waveguides may be configured to support 6 modes. Each of the input waveguides may be configured to support 3 modes. The at least one light source may be configured to excite in turn individual modes of the input waveguides.

Each of the input waveguides may be polarisation maintaining.

The system may be configured such that light propagating in any one of the input waveguides is substantially not coupled to any other one of the input waveguides.

The system may further comprise a support configured to eliminate or reduce bending of the guided-wave transition in response to bending of the waveguide apparatus. The support may be configured to eliminate or reduce bending of the multimode waveguide. The support may be a substantially rigid support. The support may be formed of a material that is more rigid than a material of the guided-wave transition. The support maybe formed of a material that is more rigid than a material of the waveguide apparatus. The support may comprise, for example, at least one of glass, silica glass, metal, steel, titanium, thermoplastic polymer, a crystalline material, a ceramic material, a polycrystalline material, a composite material. A material of the support may have a Young's modulus greater than 20 GPascal, optionally greater than 50 GPascal.

Each of the different light patterns may be substantially insensitive to bending of the waveguide apparatus. The light patterns may be substantially insensitive to bending of the waveguide apparatus as long as the waveguide apparatus is not bent tightly enough to allow light to escape from the waveguides.

The light patterns may be substantially stable even when the waveguide apparatus (for example, optical fibre apparatus) is bent. The system may be suitable for use in vivo. The waveguide apparatus may bend when it is inside the human or animal body.

The stability of the light patterns may reduce an amount of calibration needed. In some circumstances, imaging may be performed without real time calibration being used. In some circumstances, imaging may be performed without access to the output of the waveguide apparatus, which may allow imaging to be performed in vivo.

At least some of the different light patterns may be substantially orthogonal to each other. At least some of the different light patterns may form a basis set of patterns.

The different light patterns may have different distributions of intensity and/or electromagnetic field.

The different light patterns may be such that all of the target region is illuminated by the light patterns.

The different light patterns may be such that each of the different light patterns illuminates all or most of the target region. The different light patterns may be such that different ones of the light patterns illuminate different parts of the target region.

The processing of the signals from the at least one detector to obtain an image of the target region may comprise, for each of the different light patterns, combining an image of that light pattern with the signal obtained from the at least one detector for that light pattern.

The processing of the signals from the at least one detector to obtain an image of the target region may comprise ghost imaging.

The image may comprise a total internal reflection fluorescence (TIRF) image. The target region may be adjacent to a distal end of the waveguide apparatus. TIRF may be used to image structures that are placed directly on a distal facet of the waveguide apparatus.

The image may comprise a depth tomography image.

The waveguide apparatus may further comprise a further guided-wave transition. The further guided-wave transition may be positioned at the distal end of the multimode waveguide. The waveguide apparatus may be formed from an optical fibre. The guided-wave transition may be formed by tapering the optical fibre at a first position along the optical fibre. The further guided-wave transition may be formed by tapering the optical fibre at a second position along the optical fibre.

The at least one light source may be configured to excite each of the input waveguides with a plurality of different wavelengths, thereby producing a plurality of light patterns for each of the input waveguides. The further guided-wave transition may cause the light patterns to become more sensitive to wavelength. Different light patterns may be produced by using different wavelengths of light, which may increase the number of light patterns that may be produced by the system. Increasing the number of light patterns may improve the resolution of the system.

The at least one light source may be configured to excite in turn each of a plurality of combinations of the input waveguides. Exciting each combination may comprise exciting at least some of the plurality of input waveguides simultaneously using selected amplitudes and/or phases to produce a desired light pattern at the output of the multimode waveguide.

Exciting different ones of the combinations may comprise exciting different subsets of the input waveguides. Exciting different ones of the combinations may comprise exciting the same input waveguides using different selected amplitudes and/or phases.

The amplitudes and/or phases may be selected such as to form the desired light pattern. The same input waveguides, when excited with different amplitudes and/or phases, may form different light patterns. By exciting more than one input waveguide at a time, a greater number of light patterns may be formed. Using a greater number of light patterns may increase the resolution of the system.

Each light pattern may be the result of constructive and/or destructive interference between the light passing through each of the at least some of the plurality of input waveguides. The light from the different input waveguides may be combined in the guided-wave transition to form each desired light pattern.

Each desired light pattern may comprise a spot of light.

The spot of light may be positioned at a distal surface of the waveguide apparatus. The spot may provide a point light source at the distal surface of the waveguide apparatus. The use of the guided-wave transition may allow such a spot to be positioned at the distal end of the waveguide apparatus, rather than at a distance from the waveguide apparatus. The spot may be in the near field of the output of the waveguide apparatus.

The spot of light may be positioned beyond the distal surface of the waveguide apparatus. The spot of light may be positioned within the target region.

Each of the different light patterns may comprise a spot of light at a different respective position, such as to scan the spot of light across the target region.

The system may be further configured to perform a calibration process to obtain calibration data. The selected amplitudes and/or phases may be based on the calibration data.

The system may further comprise a partially reflecting element configured to partially reflect the light patterns. The partially reflecting element may be positioned at the output of the waveguide apparatus. The partially reflecting element may comprise a partially reflecting coating. The partially reflecting coating may coat a distal facet of the waveguide apparatus. The partially reflecting coating may comprise a dichroic coating. The partially reflecting coating may be configured to partially reflect light at a wavelength used to excite the single mode cores. The partially reflecting coating may be configured to transmit fluorescent light emitted from the target region in response to the light patterns.

The system may further comprises a detector configured to receive the reflected part of the light patterns and to output signals representing the reflected part of the light patterns.

The processor may be configured to determine the selected amplitudes and/or phases based on the signals representing the reflected part of the light patterns. The calibration process may comprise determining the selected amplitudes and/or phases based on the signals representing the reflected part of the light patterns.

Exciting in turn each of a plurality of combinations of the input waveguides may comprise exciting in turn each of a plurality of pairs of input waveguides. The exciting of each of the pairs may comprise exciting a first input waveguide of the pair with light of a first frequency or wavelength of light, and exciting a second input waveguide of the pair with light of a second frequency or wavelength of light.

The processing resource may be configured to process the signals from the at least one detector to obtain at least one beat frequency. The beat frequency may be at a radio frequency. The beat frequency may be between 1 kHz and 1 THz. The at least one detector may be configured to detect a signal at the beat frequency. A bandwidth of the at least one detector may be such as to detect a signal at the beat frequency.

The input waveguides may be excited with a plurality of different frequencies, thereby obtaining a plurality of different beat frequencies.

By exciting the input waveguides using different frequencies of light, and obtaining one or more beat frequencies from the signals, the number of degrees of freedom of the system may be increased, which may allow higher-resolution images to be obtained.

The beat frequencies may be stable. The beat frequencies may be substantially insensitive to movement of the waveguide apparatus.

A diameter of each of the input waveguides may be less than 100 μm, optionally less than 20 μm, further optionally less than 10 μm, further optionally less than 5 μm. A diameter of each of the input waveguides may be greater than 0.5 μm, optionally greater than 2 μm, further optionally greater than 5 μm.

The input waveguides may each be single mode or few mode cores of a multicore section of an optical fibre. A diameter of the multicore section may be big enough that the cores are separated such that they are not coupled significantly along the length of the fibre. A separation between the fibres may be dependent on how big the guided modes are in each core.

A spacing between the input waveguides may be less than 100 µm, optionally less than 20 µm, further optionally less than 10 µm, further optionally less than 5 µm.

A diameter of the multimode waveguide may be less than 500 µm, optionally less than 200 µm, further optionally less than 100 µm, further optionally less than 50 µm. A diameter of the multimode waveguide may be greater than 10 µm, optionally greater than 20 µm, further optionally greater than 50 µm.

A diameter of the multimode waveguide may be selected in dependence on a field of view that is to be measured.

The multimode waveguide may comprise a multimode core of an optical fibre. A diameter of the multimode waveguide may be selected in dependence on a refractive index contrast between a core of the multimode waveguide and a cladding of the multimode waveguide.

A diameter of the multimode waveguide may be at least 5 times greater than a diameter of each of the input waveguides, optionally at least 10 times greater.

The output of the waveguide apparatus may be an output of the multimode waveguide.

A length of the waveguide apparatus may be at least 10 cm, optionally at least 1 m. A length of the guided-wave transition may be less than 50 mm, optionally less than 20 mm, further optionally less than 10 mm.

The at least one light source may be configured to excite the input waveguides with light having a wavelength between 300 nm and 1100 nm. The at least one light source may be configured to excite the input waveguides with light having a wavelength between 10 nm and 50 µm, optionally between 200 nm and 15 µm. The at least one light source may be configured to excite the input waveguides with at least one of visible light, near-infrared light, mid-infrared light, infrared light, ultraviolet light. The at least one light source may comprise at least one coherent light source. The at least one light source may comprise at least one laser light source.

In a further aspect of the invention, which may be provided independently, there is provided a system comprising a waveguide apparatus comprising a plurality of input waveguides, a multimode waveguide, and a guided-wave transition coupling the plurality of input waveguides to the multimode waveguide; at least one light source configured to excite individually in turn each of the input waveguides, thereby generating a plurality of different light patterns in turn at an output of the waveguide apparatus, wherein the waveguide apparatus is configured to direct each of the plurality of different light patterns to a target region; and at least one detector configured to detect light transmitted, reflected or emitted from the target region in response to each of the different light patterns, and to output signals representing the detected light.

In a further aspect of the invention, which may be provided independently, there is provided a system comprising a waveguide apparatus comprising a plurality of input waveguides, a multimode waveguide, and a guided-wave transition coupling the plurality of input waveguides to the multimode waveguide; at least one light source configured to excite the input waveguides with a plurality of different sets of selected amplitudes and/or phases in turn, thereby generating a plurality of different desired light patterns in turn at an output of the waveguide apparatus, wherein the waveguide apparatus is configured to direct each of the plurality of different desired light patterns to a target region; and at least one detector configured to detect light transmitted, reflected or emitted from the target region in response to each of the different desired light patterns, and to output signals representing the detected light.

In a further aspect of the invention, which may be provided independently, there is provided a system comprising a waveguide apparatus comprising a plurality of input waveguides, a multimode waveguide, and a guided-wave transition coupling the plurality of input waveguides to the multimode waveguide; at least one light source configured to excite in turn each of a plurality of combinations of the input waveguides, wherein exciting each combination comprises exciting a respective first one of the input waveguides with a first frequency or wavelength of light and exciting a respective second one of the input waveguides with a second frequency or wavelength of light, thereby generating a plurality of different light patterns in turn at an output of the waveguide apparatus, wherein the waveguide apparatus is configured to direct each of the plurality of different light patterns to a target region; at least one detector configured to detect light transmitted, reflected or emitted from the target region in response to each of the different light patterns, and to output signals representing the detected light; and a processor configured to process the signals from the at least one detector to obtain a beat frequency for each of the combinations.

In a further aspect of the invention, which may be provided independently, there is provided a method comprising by at least one light source, exciting in turn each of a plurality of input waveguides of a waveguide apparatus, or a plurality of combinations of the input waveguides, thereby generating a plurality of different light patterns in turn at an output of the waveguide apparatus, wherein the waveguide apparatus comprises the plurality of input waveguides, a multimode waveguide, and a guided-wave transition coupling the plurality of input waveguides to the multimode waveguide; directing by the waveguide apparatus each of the plurality of different light patterns to a target region; detecting by at least one detector light transmitted, reflected or emitted from the target region in response to each of the different light patterns; and outputting by the detector signals representing the detected light.

There may be provided a method or system substantially as described herein with reference to the accompanying drawings.

Features in one aspect may be provided as features in any other aspect as appropriate. For example, features of a method may be provided as features of an apparatus and vice versa. Any feature or features in one aspect may be provided in combination with any suitable feature or features in any other aspect.

DETAILED DESCRIPTION OF EMBODIMENTS

Embodiments of the invention are now described, by way of non-limiting example, and are illustrated in the following figures, in which:

FIG. 2a is a proximal end view of an optical fibre of FIG. 1;

FIG. 2b is a distal end view of the optical fibre of FIG. 1;

FIG. 3a is an image of the proximal end of the optical fibre of FIG. 1;

FIG. 3b is an image of the distal end of the optical fibre of FIG. 1;

FIG. 9 shows a) a plurality of micrographs of a further imaged object and b) ghost image outputs corresponding to the micrographs of FIG. 8a.

FIG. 1 is a schematic illustration of an imaging system 10 in accordance with an embodiment.

Figure 1:
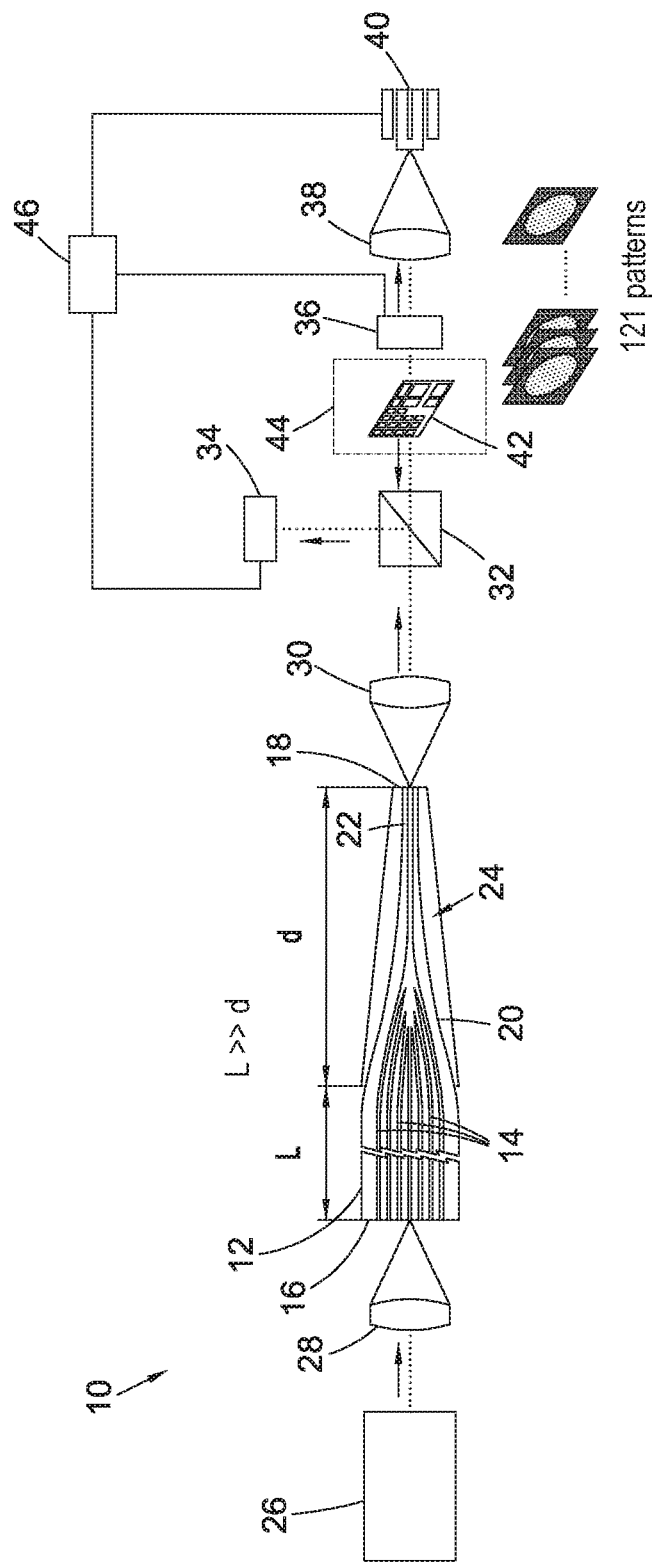
FIG. 1 is a schematic illustration of a system according to an embodiment.

The imaging system 10 comprises an optical fibre 12 which is formed by tapering a multicore optical fibre. In the present embodiment, the optical fibre 12 is as described in Harikumar K. Chandrasekharan, Frauke Izdebski, Itandehui Gris-Sánchez, Nikola Krstajić, Richard Walker, Helen L. Bridle, Paul A. Dalgarno, William N. MacPherson, Robert K. Henderson, Tim A. Birks & Robert R. Thomson, Multiplexed single-mode wavelength-to-time mapping of multimode light, Nature Communications 8, 14080 (2017).

The multicore optical fibre comprises an 11×11 square array of single mode cores 14. The single mode cores 14 are single mode for wavelengths between about 470 nm and 610 nm. In other embodiments, the single mode cores 14 may be single mode for wavelengths of above around 400 nm, 500 nm, or 600 nm. The single mode cores 14 are arranged in a square grid with a spacing of 10.53 µm. Each of the single mode cores 14 is 1.63 µm in diameter. The single mode cores 14 are formed from germanium-doped silica. A cladding material for the multicore optical fibre is pure silica. The numerical aperture of the cores is 0.22 and the fibre's outer diameter is 200 µm.

In further embodiments, a spacing between the cores may be any suitable spacing that stops significant coupling of light between single mode cores after propagating down the lengths of the fibre. In some embodiments, the single mode cores are positioned more closely together by reducing the wavelength, increasing the core-cladding index contrast and/or reducing the core size.

Although in the present embodiment, the plurality of cores 14 of the multicore fibre are single mode, in other embodiments each core from the multicore fibre may support a small number of modes, for example 3 or 6 spatial modes FIG. 2a is a schematic illustration of an end view of a proximal end 16 of the optical fibre 12, showing the plurality of single mode cores 14.

The optical fibre 12 is tapered at a distal end 18 to form a photonic lantern transition 20. In the present embodiment, the photonic lantern transition 22 is formed by placing the multicore fibre inside a low index capillary, tapering the multicore fibre, and cleaving the tapered multicore fibre near the middle of the taper. The cleaved end may be considered to form a traditional step-index core-clad multimode waveguide 22, where the core of the multimode waveguide 22 is formed out of the tapered multicore fibre, the cladding is formed out of the tapered low index capillary, and the individual cores of the multicore fibre are now too small to properly guide light.

FIG. 2b is a schematic illustration of an end view of the distal end of the optical fibre, which shows the multimode core 22. The multimode core 22 is larger than each of the single mode cores 16.

The portion of the optical fibre 12 that comprises the single mode cores 14 has a length L. The photonic lantern transition 20, including the section of multimode core 22, has a length d which is much less than L. For example, L may be a metre or more while d may be a few millimetres or tens of millimetres. Dimensions in FIG. 1 are not shown to scale.

A photonic lantern is a guided-wave device which in its ideal case couples an array of N single mode cores at one end to a multimode core supporting N guided modes at the other, where the ends are linked by an adiabatic transition. In such a transition, light injected into one core at the single mode end may be considered to slowly evolve into a coherent mode at the multimode end. The coherent mode has a specific amplitude and phase profile at the output from the lantern transition. Examples of photonic lanterns and methods of forming photonic lanterns are described in Birks, T. A., Gris-Sanchez, I., Yerolatsitis, S., Leon-Saval, S. G. & Thomson, R. R. The photonic lantern. Adv. Opt. Photon. 7, 107 (2015)

In the photonic lantern transition 20, the waveguide changes smoothly and continuously from the single mode cores 14 to the multimode core 22. Light that is input into any one of the single mode cores 14 may be distributed across most or all of the modes in the multimode core 22 to form a specific pattern of light.

It has been found that, in a photonic lantern that is formed by tapering a multicore fibre at one end, very specific multimode patterns of light may be generated at the output at the distal end of the photonic lantern when light is individually coupled into each single mode core at the proximal end of the photonic lantern, as long as the single mode cores 14 are not significantly coupled over the length of fibre used. Different light patterns may be formed by exciting different ones of the single mode cores 14. The light patterns formed by different optical fibres having the same design may be similar, but the exact light patterns formed may be unique to a given multicore fibre and guided-wave transition. For example, two photonic lanterns may be fabricated to the same design by tapering and cleaving a length of multicore fibre. However, the position where the tapered section is cleaved may not be exactly the same for both lantern transitions, causing the light patterns to differ at least slightly.

FIG. 3a is an image of the input (proximal) end 16 of the optical fibre 12 when light is input into the distal end 18 of the optical fibre. FIG. 3a shows the square array of single modes of the 121 core multicore fibre. FIG. 3a demonstrates that light that is input into the multimode core 22 may be coupled into most if not all of the single mode cores 14. Scale bars in FIGS. 3a and 3b represent 10 µm.

FIG. 3b shows the tapered output of the photonic lantern 20 at the opposite end. FIG. 3b is an image of the output (distal) end 18 of the optical fibre 12 when light is input into one of the single mode cores 14. FIG. 3b shows that a specific pattern of light is produced at the distal end 18 when light is input into a particular one of the single mode cores 14. Different patterns may be produced when different ones of the single mode cores 14 are excited. FIG. 3b is discussed further below with reference to the imaging method of FIG. 4.

A rigid support 24 surrounds the photonic lantern transition 20 and multimode core 22. In the present embodiment, the rigid support is a glass capillary. In other embodiments, the rigid support 24 may be formed any suitable material that is more rigid than the waveguide apparatus. For example, the rigid support 24 may be formed of silica glass, a metal or a thermoplastic polymer. The rigid support may be a 3D printed steel or titanium sleeve, or a crystalline, ceramic or polycrystalline sleeve that may be manufactured using laser processing techniques.

The photonic lantern transition 20 and multimode core 22 are packaged with the rigid support 24 in such a way as to ensure that the photonic lantern transition 20 and multimode core 22 are highly stable. For example, if the optical fibre 12 is bent, the photonic lantern transition 20 and multimode core 22 may not bend due to the presence of the rigid support 24.

The system of FIG. 1 further comprises a coherent light source 26. In the present embodiment, the coherent light source 26 is a laser light source that is configured to provide laser light with a wavelength of 514 nm. In other embodiments, any appropriate coherent light source may be used. The laser light may be, for example, visible, infrared or ultraviolet light.

The system of FIG. 1 further comprises two detectors 34, 36 and a camera 40. In further embodiments, a different imaging device may be used in place of the camera 40, for example a scanning galvanometer system having a single pixel. The detectors 34, 36 are low-noise detectors. In some embodiments, the detectors 34, 36 may be single-photon sensitive.

The system of FIG. 1 further comprises an input lens 28 positioned between the coherent light source 26 and the proximal end 16 of the optical fibre 12; an output lens 30 positioned between the distal end 18 of the optical fibre 12 and a target region 44; and an imaging lens 38 positioned between the target region 44 and the camera 40. In other embodiments, each of the lenses 28, 30, 38 may comprise a combination of lenses or other optical components. Any suitable combination of optical components may be used in place of the lenses 28, 30, 38.

The system of FIG. 1 further comprises a beam splitter 32 configured to split light from the distal end 18 of the optical fibre 12 such that part of the light is incident on the first detector 34 and another part of the light is incident on the target region 44.

The system of FIG. 1 further comprises a processor 46. In the present embodiment, the processor 46 forms part of a personal computer (PC) or laptop. In other embodiments, the processor 46 may form part of any computing system.

Figure 4:
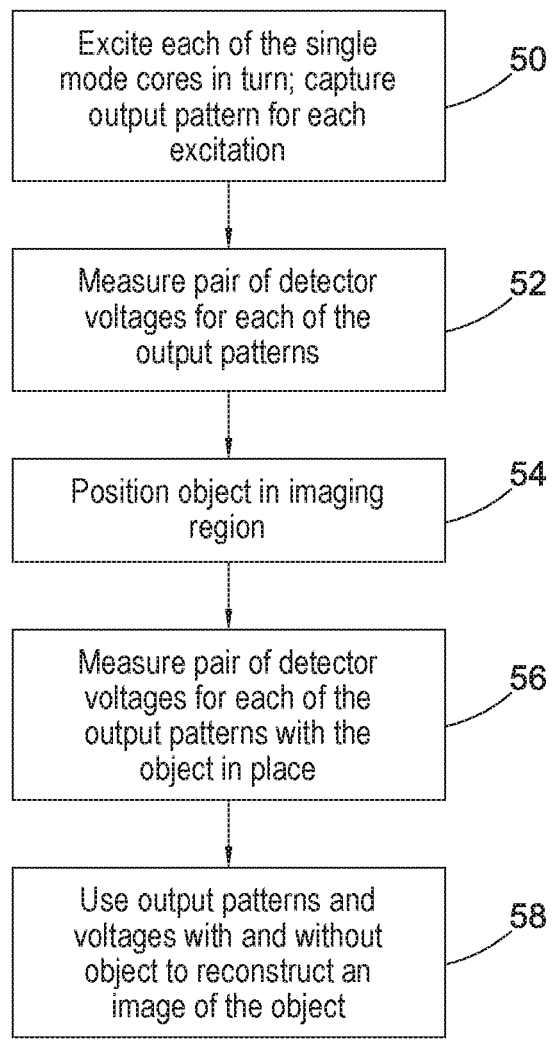
FIG. 4 is a flow chart illustrating in overview a method of an embodiment.

FIG. 4 is a flow chart illustrating in overview a method of operating the system of FIG. 1 to image an object 42 that is positioned within the target region 44.

At stage 50 of FIG. 4, laser light from the coherent light source 26 with a wavelength of 514 nm is injected individually into each single mode core 14 at the proximal end of the optical fibre 12 via the input lens 28. Each of the single mode cores 14 is excited in turn.

When light is injected into one of the single mode cores 14, light propagates in that core 14 without significantly coupling to any of the other single mode cores 14. Any coupling into other single mode cores 14 may be negligible or sufficiently low for the application. The light is distributed over a plurality of modes in the multimode core 22 and forms a light pattern, for example a light pattern as illustrated in FIG. 3b.

It has been observed that by exciting one single mode core at the un-tapered end of the optical fibre 12, a specific pattern of light may be generated at the multimode output 20 from the optical fibre 12, and the pattern is insensitive to movement of the optical fibre 12. For excitation of a given one of the single mode cores 16, the pattern generated at the distal end of the optical fibre 12 in response to excitation of that single mode core may be considered to be insensitive to bending of the multicore fibre, as long as the photonic lantern transition 20 itself does not bend. In the present embodiment, the photonic lantern 20 and multimode waveguide 22 are prevented from bending by the rigid support 24.

Light emitted from the distal end of the optical fibre 12 is collected using the output lens 30 and imaged to a position in the target region 44 in which the object 42 is to be placed. The object 42 and second detector 36 are not present during stage 50.

The imaging lens 38 is used to re-image the first image plane to the camera 40. The camera 40 captures each of the output patterns that are emitted from the optical fibre 12 when light is coupled into each single mode core 14 of the optical fibre 12 individually.

As shown in FIG. 4b, by imaging the output of the photonic lantern 20 with sufficient magnification onto a camera 40, it may be possible to capture the light distribution as an intensity pattern. Using the optical fibre 12 of the present embodiment, 121 unique intensity patterns may be generated at the tapered end by coupling light into each single mode core 16 at the un-tapered end of the optical fibre 12 one at a time. For an ideal photonic lantern 20, the 121 different intensity patterns are orthogonal in their electromagnetic field distribution but are not unique in their intensity distribution. The intensity patterns are recorded by the camera.

The imaging with the camera 40 is such that the intensity patterns are known with sufficient resolution and precision to allow accurate reconstruction of the system.

Stage 50 results in a set of 121 intensity pattern images, one for each of the single mode cores. The 121 intensity pattern images are stored by the processor 46.

At stage 52, the second detector 36 is placed between the target region 44 and the imaging lens 38. There is still no object 42 in the target region 44.

Laser light from the coherent light source 26 with a wavelength of 514 nm is injected individually into each single mode core 14 at the proximal end of the optical fibre 12 via the input lens 28. Light emitted from the distal end of the optical fibre 12 is collected using the output lens 30 and imaged to a position in the target region 44 in which the object 42 is to be placed. Part of the light emitted from the distal end of the optical fibre 12 is reflected by the beamsplitter placed between the output lens 30 and the target region 44, and is incident on the first detector 34.

The first detector 34 detects the light that is reflected by the beamsplitter 32 and outputs a first detector voltage D1 in dependence on the amount of light detected. The second detector detects light that is transmitted through the target region 44 and outputs a second detector voltage D2 in dependence on the amount of transmitted light detected. The detectors 34, 36 have low enough noise to provide high accuracy measurements of the powers of light. In some embodiments, the detectors 34, 36 may be sensitive to single photons, or at least extremely sensitive and low noise.

The processor 46 uses the first detector voltage D1 and second detector voltage D2 to obtain a ratio of detector voltages D1/D2 for the detectors 34, 36. The processor 46 obtains and stores a respective ratio of detector voltages D1/D2 for each multicore fibre input, i.e. for each of the different light patterns resulting from excitation of each one of the single mode cores 14.

A self-referencing arrangement of detectors 34, 36 as described above may enable a ratiometric measurement to be obtained, which may thereby circumvent time varying fluctuations in the detector readouts.

Stages 50 and 52 may be described as calibration steps. At stage 54, after the calibration steps are complete, an object 42 is placed in the target region 44 at the first image plane of the output from the optical fibre 12.

At stage 56, 514 nm laser light is again injected individually into each one of the single mode fibres 14, and the D1/D2 ratio is remeasured for each multicore fibre input. It may be expected that the ratio D1/D2 of light detected by the detectors 34, 36 with the object 42 present in the target region may be different from the ratio D1/D2 that was detected when the object was not present.

The processor 46 stores a respective ratio of detector voltages D1/D2 for each of the different light patterns resulting from excitation of each one of the single mode cores 14 when the object 42 is present in the target region.

The D1/D2 ratios measured with and without the object 42 are affected by the overlap of the projected pattern and the spatial transmission properties of the object. These differences may provide an ability to reconstruct the object.

At stage 58, the processor 46 uses the images of the different patterns from stage 50, the D1/D2 ratios without the object from stage 52, and the D1/D2 ratios with the object from stage 56 to reconstruct an image of the object, for example by using a ghost imaging method. The ghost imaging method may be similar to a method described in, for example, Baoqing Sun, Stephen S. Welsh, Matthew P. Edgar, Jeffrey H. Shapiro, and Miles J. Padgett, "Normalized ghost imaging," Optics Express 20, 16892-16901 (2012). In some embodiments, the imaging method may be similar to a method used in Reza Nasiri Mahalati, Ruo Yu Gu, and Joseph M. Kahn, "Resolution limits for imaging through multi-mode fiber," Opt. Express 21, 1656-1668 (2013), in which a multimode fibre is used to project quasi-random patterns onto an object, a proportion of the light reflected from the object is then transmitted back up the fibre and from a knowledge of the patterns and the powers, the object may be reconstructed.

Ghost imaging may comprise methods in which a plurality of different light patterns are used to illuminate an unknown object, and the transmitted (or reflected) light is measured using a detector, for example a single-element detector. For each of the light patterns, the signal produced by the detector when the object is illuminated by a given light pattern may be considered to be representative of how much of that light pattern is transmitted (or reflected). By collecting the signals for a large number of light patterns, it may be possible to determine the shape of the object. It has previously been known to perform ghost imaging with, for example, a series of laser speckle patterns.

In the embodiment of FIG. 4, the light patterns used to perform ghost imaging are the patterns generated by excitation of the different single mode cores 14. The modes generated by a photonic lantern are used for image reconstruction.

In a demonstration of proof of principle, a razor blade and a chrome plated USAF resolution target were each imaged using the system of FIG. 1.

Figure 5:
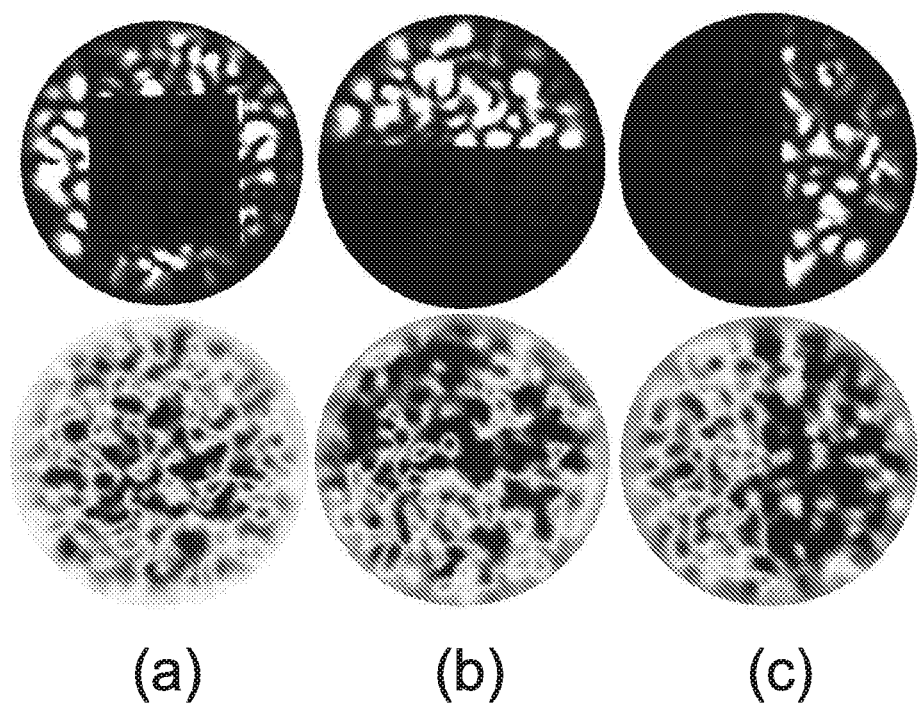
FIGS. 5a-5c show a set of camera images and a set of reconstructed images using intensity patterns generated by a photonic lantern.

FIGS. 5a-5c show reconstructed images of objects using the system of FIG. 1 and the method of FIG. 4. For each of three objects (a), (b), (c), a top row image shows the object obtained using camera 40 in FIG. 1, and a bottom row image shows an image of the object that was reconstructed using the 121 intensity patterns generated by the optical fibre 12 comprising the photonic lantern 20. The object used in (a) is a square feature from a USAF target. The object used in (b) is a knife edge in horizontal orientation. The object used in (c) is a knife edge in vertical orientation.

The proof of principle results shown in FIGS. 5a-5c are obtained using only 121 intensity patterns. The results may be considered to highlight the potential of using the modes of the photonic lantern for imaging applications. By increasing the number of cores in the multicore fibre, the resolution of the reconstructed images may be improved considerably. For example, the multicore fibre may comprise thousands or tens of thousands of single mode cores. Injecting light into individual ones of the single mode cores may enable thousands or tens of thousands of intensity patterns to be formed. By increasing the number of cores in the multicore fibre, the resolution of the reconstructed images may be improved considerably from those shown in FIGS. 5a-5c.

In the system illustrated in FIG. 1, light detection is performed distally. In other embodiments, light detection may be performed proximally (for example, for in vivo application) using the same basic concept as that described with reference to the system of FIG. 1.

In some embodiments, the concept described above with reference to FIG. 1 is extended to endomicroscopy. The optical fibre 12 forms part of or is inserted into an endoscope which may be introduced into the body of a patient, for example into the patient's lung.

The individual patterns generated by the photonic lantern are projected onto an object 42, and a measurement is made of the amount of light (either reflected or fluorescence) that is transmitted back up the optical fibre 12 for each pattern. Algorithms such as those used for ghost imaging may then be used to reconstruct the object 42.

Using the optical fibre technology described above, the theory of compressive sensing may be leveraged to provide a compressive microendoscopic imaging modality.

Tapering the multicore fibre down to a narrow waist to form the lantern may allow true in vivo microendoscopy to be achieved. For example, it may be possible to image bacteria, not just detect them. In some embodiments, there may be the potential to achieve imaging of fluorescence biomarkers with intracellular detail. There may be the possibility for super-resolution endomicroscopy.

The photonic lantern structure may enable the projection of different stable intensity patterns that are substantially insensitive to fibre movement and bending provided that the photonic lantern transition length is packaged rigidly. Since the transition may be designed and fabricated to be as short as a few mm, it may be packaged in such a way to ensure that it is highly stable.

In embodiments, the light patterns may remain stable as long as the fibre is not bent tightly enough to allow light to escape from the core. If the fibre is bent too tightly, then light may escape from the core and the power of light emitted from the distal end may not be known (although in some circumstances this information may be obtained from an amount of light reflected from the distal end).

Once the relationship between the pattern generated at the output of the optical fibre 12 and the single mode excitation is calibrated, then this relationship may be considered to be known regardless of how the multicore fibre itself is manoeuvred, as long as the single mode cores 14 exhibit negligible coupling over the length L of multicore fibre used.

It may therefore be possible to perform imaging without having access to the distal end of the optical fibre 12. For example, the light patterns generated by injecting light into each of the single mode cores 14 in turn may be obtained before inserting the optical fibre 12 into a patient, and it may be assumed that those patterns are stable even if the optical fibre 12 bends while it is in situ. This contrasts to some known methods in which if the optical fibre moves, the patterns need to be recalibrated.

The method described above may enable high fill-factor, high-resolution endomicroscopy in vivo and in situ, without requiring bulky fibre bundles or fragile distal scanning tips. In known methods of imaging using a coherent fibre bundle, an object or region to be imaged is sampled at sampling points that are spaced apart in accordance with the spacing of the fibre cores, and therefore the fill-factor obtained may be relatively low. The use of a photonic lantern or similar transition may enable a higher fill-factor and higher resolution to be obtained.

High resolution imaging may be performed by using as many different patterns in as small an area as possible at the distal end. In some embodiments, high resolution may be achieved by maximising an index contrast between the core and the cladding (for example, by using a cladding that is air or vacuum). In some embodiments, high resolution may be achieved by tapering the distal end down until reaching the minimum possible size before modes start to be unguided.

Low numerical aperture cores that are single mode or have few modes are coupled to a multimode core that has high numerical aperture.

The system of FIG. 1 may operate over a wide spectral bandwidth. The bandwidth may in some circumstances be limited by the bandwidth over which negligible coupling between cores over the length of the multicore fibre may be obtained and/or by the bandwidth over which either single or few mode operation of the individual cores may be obtained.

Properly designed devices may enable very efficient operation e.g. very efficient delivery of pump light, and very efficient collection of signal light to detectors.

When compared to methods in which a single mode or multimode fibre with a scattering distal tip is used to provide compressive sensing using characterised speckle patterns, some embodiments may provide much higher throughput in the return path due to the use of multimode signal collection at the distal end.

In the case of a photonic lantern, light from the object that is collected by the multimode core may be efficiently coupled into most (or all) of the single mode cores and transmitted to the proximal end for processing. In the case of a scattering distal tip attached to a single mode fibre (or a multicore fibre with single mode cores), the coupling efficiency of light from the scattering tip to the single mode core may be much lower compared to the case of the photonic lantern.

Multimode fibres support multiple spatial modes, and therefore accept light from more angles than single mode fibres. This may make multimode fibres much more efficient at capturing the types of signals, for example multimode reflected and incoherent fluorescent signals, that may be generated by systems as described above.

In some embodiments above, reflected or fluorescent light is returned to the proximal end of the optical fibre via the photonic lantern and single mode cores. In other embodiments, light may be collected from the distal end of the optical fibre by a further core or fibre.

In some embodiments, there may be potential for an optical fibre having a photonic lantern transition as described above to be configured for use in total internal reflection (TIRF) mode. In TIRF mode, the distal end 18 is processed such that the generated pattern internally reflects from a surface where the sample is placed, which may be a distal facet of the optical fibre. The use of TIRF mode may give extreme sectioning of a sample.

In a further embodiment, the optical fibre 12 may be used to perform depth tomography. To perform depth tomography, the system may be configured to send out patterns of light in a pulsed fashion, and measure the times that the pulse is returned to the distal end. This may provide information in a manner similar to that described in Ming-Jie Sun, Matthew P. Edgar, Graham M. Gibson, Baoqing Sun, Neal Radwell, Robert Lamb & Miles J. Padgett, Single-pixel three-dimensional imaging with time-based depth resolution, *Nature Communications* 7, 12010 (2016).

The depth information obtained may be highly dependent on the timing resolution of the detector. The detector may be a single-photon detector with a resolution of a few ps.

Another approach may be to send broadband light (either pulsed or continuous wave) down one core at a time, and perform an optical coherence tomography measurement on the returned outputs of the single-mode cores for each input core. This may provide greatly enhanced resolution on the micrometer scale.

In some embodiments, there may be the possibility to exploit higher degrees of freedom, such as wavelength, phase and/or polarisation to increase the number of patterns that can be generated.

In the embodiment described above with reference to FIG. 4, the multiple cores 14 at the proximal end of the optical fibre 12 are single mode. In other embodiments, each of the cores may be capable of being excited in a small number of modes. A lantern formed from few-mode cores may be used to increase the number of patterns that can be generated, if precise and pure excitation of the modes is used. Each mode of each core may be excited in turn. A system using few mode excitation may be a more complicated system than a system using single mode excitation, since it may make use of precise mode selective excitation.

In a further embodiment, a multi-taper transition is created at the distal end 18. In an example of a multi-taper transition, the optical fibre is tapered at the distal end 18 as shown in FIG. 1, but then widens again before narrowing again, such that the widened section is an array of substantially uncoupled cores and the narrowed section is an effective multimode core. The use of the multi-taper transition may result in patterns generated at the distal end being highly wavelength-sensitive. The use of a multi-taper transition may offer a way to increase the number of patterns possible, by tuning the input wavelength. In the system of FIG. 1, the light patterns produced may be relatively insensitive to wavelength. In contrast, the multi-taper transition may produce patterns that are much more sensitive to wavelength. Therefore, a change in wavelength may be used to produce additional patterns, which may improve the resolution of the image obtained. Double or multiple tapering may allow tuning wavelength to provide an additional degree of freedom to increase the number of patterns.

In some embodiments, controlled mechanical deformation of a distal-end structure including more than one taper may be used to generate more patterns.

In some embodiments, the output of the optical fibre comprises an untapered multicore fibre. For example, a multicore fibre may narrow to form a photonic lantern then widen again into multicore fibre.

In embodiments such as that described above with regard to FIG. 1 and FIG. 4, a guided-wave transition (such as a photonic lantern) is used to project different patterns of light onto an object. Light is coupled into each core 14 of the device, one core at a time. The system is calibrated. The pattern of light that is generated at the output when coupling light into each core is known. These patterns are projected onto the object and by measuring the amplitudes of light (either fluorescence generated, reflected light, or transmitted light), it is possible to build up an image of the object using a variety of algorithms.

In such embodiments, coupling is only to one core at a time. As such, the pattern of light at the output is stable, as long as the cores are not coupled significantly over the length of fibre used.

In a further embodiment, coherent light is coupled into multiple cores of a guided-wave transition simultaneously. Phase and amplitude control on each mode is used to generate a desired intensity profile at the output of the transition.

It has been described above that injecting light into each of the single mode cores 14 results in a respective intensity pattern for each of the single mode cores. If light is injected into more than one of the single mode cores using controlled phases and amplitudes, a desired intensity pattern may be formed at the distal end 18 of the optical fibre 12. For example, a spot may be formed.

In some embodiments, light is coupled into multiple cores of a multicore fibre simultaneously. The phases and amplitudes of the light in each core are controlled to generate a desired distribution of light at the output. The cores may be polarisation maintaining.

In some embodiments, the desired distribution of light comprises a spot at the distal end 18 of the optical fibre 12. The spot may be considered to provide a point light source. The spot may be scanned by changing the phases and/or amplitudes of the single mode cores 14. Unlike in some known methods, the spot may be provided on the distal end 18 itself instead of in the far field.

In some embodiments, the desired distribution of light may comprise a spot at some distance from the end facet of the optical fibre 12. For example, a spot may be generated in the target region 44. The spot at some distance from the facet may be scanned by appropriate phase and amplitude control.

One method by which an arbitrary array of spots with desired phases and amplitudes may be generated is described in RA Vicencio et al., Observation of Localized States in Lieb Photonic Lattices, *Phys Rev Lett* 114 (24), 245503 2015 Jun. 15, in which spatial light modulators are used to generate a 4 spot pattern with a 0-pi-0-pi phase profile. The basic techniques outlined in Vicencio et al may also be extended to generate much more complex amplitude and phase profiles for the input to the fibre.

In embodiments in which multiple single mode cores 14 are excited simultaneously, the relative phases of the light in each core are expected to change as the fibre is adjusted (if an optical fibre being used). Thus relative phases of the light are monitored in real time and adjusted to correct for movement of the fibre.

Dynamic phase correction in multicore fibre systems has been demonstrated using spatial light modulators (SLMs), in papers such as Kim, Y., Knight, J., Warren, S., Neil, M., Paterson, C., Stone, J., Dunsby, C. and French, P., 2016. Adaptive multiphoton endomicroscope incorporating a polarization-maintaining multicore optical fiber. *IEEE Journal of Selected Topics in Quantum Electronics*, 22 (3), 6800708. The implementation described in the paper by Kim et al had access to the output end. Holography using a reference beam was used to measure the phase at the output and correct for any phase perturbations.

In some embodiments, light is coupled into multiple cores in an endoscopic application in which there is no direct access to the distal end of the endoscope. The distal end 18 of the photonic lantern is coated with a partially reflective coating. Light reflected from the partially reflective coating is used to calibrate the system in real time. Light reflected from the partially reflective coating is used to provide amplitude and/or phases to be used in exciting multiple single mode cores to obtain a desired pattern.

If light is injected into one single mode core 14 of the multicore fibre, it will travel down the multicore fibre without coupling significantly to the other single mode cores 14 until it reaches the photonic lantern 20. It will then generate a specific pattern of light at the output 18 of the photonic lantern transition. Since the distal end 18 of the photonic lantern transition is coated with a partially reflective coating, the pattern of light is partially reflected and will couple to a set of (in this embodiment, all) the single mode cores on the way back up the fibre. By coupling to one core at the input, the reflected light from the core couples to some or all cores on the way back up the fibre.

In the embodiment in which multiple cores are excited simultaneously, the reflected light from the multiple cores interferes in the lantern transition and alters the distribution of light across the cores. The relative phases of the light at the distal end directly determines the distribution of the reflected light that is measured at the proximal end.

In an embodiment, the pattern of light measured at the proximal end is calibrated and relates to the pattern generated at the output. The information may be used to correct the phases in real time.

In one embodiment, the partially reflective coating is a dichroic coating. A fluorescence dye is used on tissue to be imaged. The dichroic coating reflects 95% of the light at the excitation wavelength. The dichroic coating reflects only a tiny amount of light at a fluorescence wavelength of the fluorescence dye.

Only 5% of the excitation light exits the multimode end of the optical fibre, and only a maximum of 5% of the light that exits the multimode end would be able to re-enter the multimode end.

A camera positioned at the proximal end of the optical fibre is used to detect the pattern of light at the excitation wavelength that is reflected from the dichroic coating. Because only a small amount of light at the excitation wavelength is transmitted by the dichroic coating, the pattern of light detected at the proximal end is very insensitive to the amount of excitation light that is reflected from the object. The system further comprises a dichroic positioned in front of the camera at the proximal end of the optical fibre, so that the camera is only looking at the pattern of light at the excitation wavelength.

Since a lot of excitation light is available, it may make little difference to reflect 95% of it at the multimode end. Since the coating is dichroic and is configured to pass almost all of the light at the fluorescence wavelength, fluorescence from the sample is efficiently accepted into the multimode end of the device.

Figure 6:
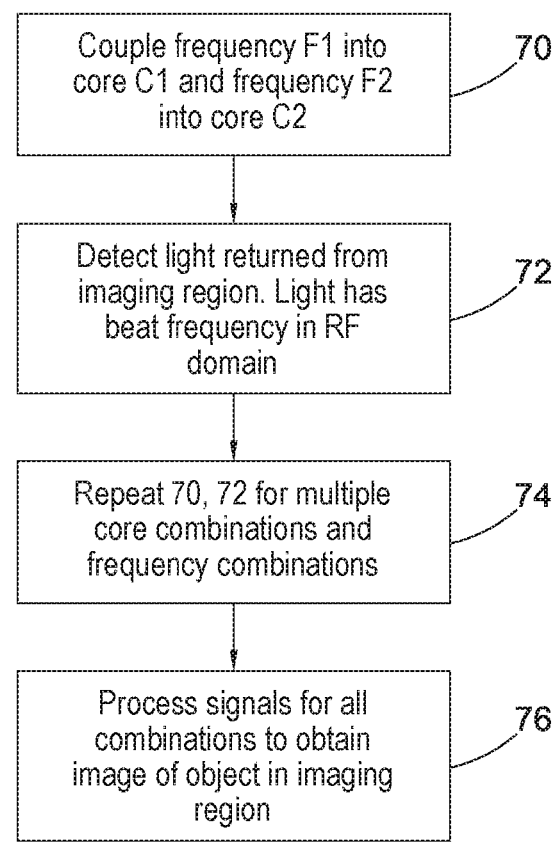
FIG. 6 is a flow chart illustrating in overview a method of a further embodiment.

FIG. 6 is a flow chart describing in overview a method of an embodiment in which different wavelengths are coupled into each of two or more of the single mode cores 13. Beat frequencies are used to obtain an image.

At stage 70 of FIG. 6, the coherent light source 26 produces a beam of light having a first frequency F1. An acousto-optic modulator is used to generate a diffracted beam which is Doppler shifted in frequency from the first frequency by a desired amount. The diffracted beam has a second frequency F2. Using the acousto-optic modulator gives two beams with a desired frequency difference (F1−F2).

The first frequency of light F1 is coupled into a first one of the single mode cores C1. The light in C1 propagates down the multicore fibre. The multicore fibre is designed to be uncoupled over the length L of fibre used, so the coupling into any of the other single mode cores is negligible. The light from C1 propagates into the lantern transition 20 and forms a first pattern of light at the output 18.

The second frequency of light F2 is coupled into a second one of the single mode cores C2. The light from C2 propagates down the multicore fibre with negligible coupling into any other of the single mode cores. The light from C2 propagates into the lantern transition 20 and forms a second pattern of light at the output 18. The two patterns of light overlap in some regions.

The intensity of the overlapping regions varies at the beat frequency (F1−F2). In the present embodiment, the beat frequency (F1−F2) is chosen to be in the radio frequency domain.

Light from the two patterns of light is incident on an object in the target region, and part of the light is reflected. At stage 72, a detector at the proximal end of the optical fibre 12 detects a signal returned up the fibre from the target region 44. The detector has sufficient bandwidth to see a signal at the beat frequency. The detector may be a high speed photodetector. It is expected that the frequency of the beat note will be quite insensitive to bending of the fibre. Bending may generally only induce up to kHz level phase variations between the modes, which may be negligible compared to the RF beat frequency, which may be for example MHz or GHz.

At stage 74, stages 70 and 72 are repeated for different pairs of cores. Using this approach, one may investigate the strengths of the signals that are generated by coupling light into each pair of cores, one at a time, thus generating $(((n^2)-n)/2)$ individual pieces of information, rather than n bits of information as is the case in the embodiment of FIG. 4.

At stage 76, the processor 46 processes signals from each pair of cores to reconstruct an image of the object. The object is constructed using similar algorithms as those used in stage 56 of FIG. 4.

The embodiment of FIG. 6 uses a basic idea for using more than one frequency to obtain additional information by forming additional patterns (which in the case of FIG. 6 are beat-frequency patterns formed by simultaneously exciting two cores with different frequencies).

More advanced implementations of the basic idea used in FIG. 6 may also be envisaged.

In one embodiments, two mode-locked lasers are used to provide light. The two mode-locked lasers have slightly different cavity lengths. The mode-locked lasers may be, for example, carrier-envelope-phase stabilised lasers.

Individual modes of the first mode-locked laser may be coupled into each core of the fibre. One may then couple individual modes of the other mode-locked laser, which deliberately has a slightly different cavity length and therefore slightly different mode frequencies, into each core of the fibre.

The modes of the mode-locked lasers are longitudinal modes. The second mode-locked laser has a different cavity length from the first mode-locked laser and therefore the longitudinal mode spacing and longitudinal mode frequencies of the second mode-locked laser are different from those of the first mode-locked laser.

At the output, each pair of cores may generate a modulated pattern with a distinct beat frequency. By recording the RF spectrum of the returned light, one may then immediately record the powers of these notes. This idea borrows some concepts from dual comb spectroscopy.

In one embodiment, two mode-locked lasers are used as light sources. A first mode from the first mode-locked laser is coupled into a first core. A second mode from the first mode-locked laser is coupled into a second core. A third mode from the first mode-locked laser is coupled into a third core, and so on up to an Nth mode from the first mode-locked laser which is coupled into an Nth core.

Then a first mode from the second mode-locked laser is coupled into the first core. A second mode from the second mode-locked laser is coupled into the second core. A third mode from the second mode-locked laser is coupled into the third core, and so on up to an Nth mode from the second mode-locked laser which is coupled into the Nth core.

In this embodiment, each pair-wise combination of cores is represented by a unique beat frequency.

In further embodiments, the concept may be used for groups of modes. Groups of modes may be coupled into each core, Each pair of cores may then be represented by a group of beat frequencies.

The use of multiple frequencies, and the use of beat frequencies, may allow increased information to be obtained from a given number of cores when compared to an embodiment in which only one core at a time is excited.

In embodiments described above, a photonic lantern is used to couple an array of single mode cores to a multimode core. In other embodiments, any suitable guided-wave transition may be used, for example any suitable single-modes-to-multimode or few-modes-to-multimode guided-wave transition.

In some embodiments, mode-selective photonic lanterns may be used to generate light patterns that may be well matched to the spatial modes of the individual cores. A mode-selective photonic lantern may be, for example, as described in S Yerolatsitis, K Harrington, R R Thomson, T A Birks, Mode-selective Photonic Lanterns from Multicore Fibres, Optical Fiber Communication Conference OSA Technical Digest (online) (Optical Society of America, 2017), paper Tu3J.6.

A photonic lantern may be considered to comprise an adiabatic transition from an array of single mode core fibres to a single multimode core. Experiments have been performed using a fibre photonic lantern that is formed by jacketing a 121 core fibre with fluorite and then drawing it down to a diameter at which all of the cores are merged to form a multimode end of the lantern. The adiabatic transition means that when a single core of the multicore array is excited by laser light, the output of the multimode end of the lantern comprises a coherent superposition of the lowest order spatial modes guided by the unified core.

Ghost imaging is a technique developed from dual photography, in which a light field used to illuminate a scene is sequentially altered to increase an amount of information recorded by a camera (see, for example, Sen. P et al Dual photography in ACM Transactions on Graphics 24, 745-755 (ACM Press, 2005). Ghost imaging takes a dual photography technique a step further by splitting the illuminating light into two parts. The two parts of the illuminating light are usually dubbed the reference beam and the signal beam. Spatial information is recorded only from the reference beam (see, for example, *Fourier Optics and Computational Imaging* 52, 293-299 (John Wiley & Sons Ltd, 2015)). An object to be imaged is placed in the signal beam. An intensity of light reflected (or transmitted) by the object may be measured by a spatially naïve bucket detector.

Figure 7:
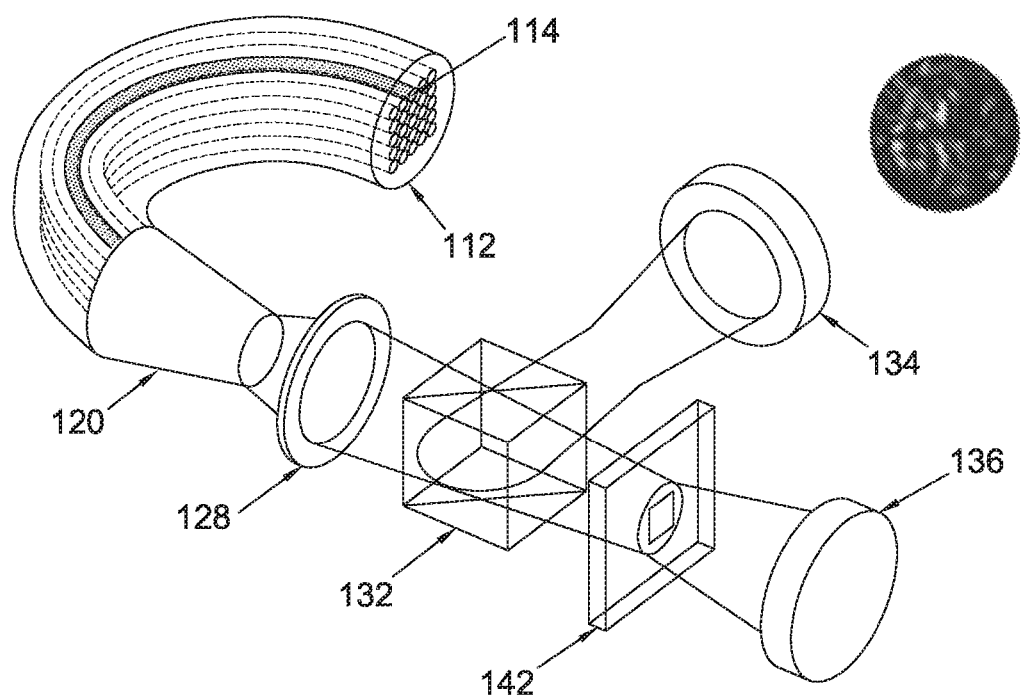
FIG. 7 is a schematic illustration of a system according to an embodiment.

FIG. 7 is a schematic illustration of an apparatus in accordance with an embodiment. A selected core 114 of a multicore optical fibre 112 is excited. Light passes through the excited core into a photonic lantern 120, through a lens 128 and into a beamsplitter 132. From the beamsplitter, the light is split into a reference beam and a signal beam. An object 142 is placed in the path of the signal beam, which is then detected by a first detector 136. The reference beam is detected by a second detector 134. By illuminating each core of the photonic lantern, the illumination for ghost imaging is provided.

In order to obtain images of objects, data collected from photodetectors 134, 136 was combined with images of supermodes according to the following algorithm:

$$O_i(x, y) = \left(\frac{S_i}{R_i} - \frac{\langle S \rangle}{\langle R \rangle}\right)(I_i(x, y) - \langle I(x, y) \rangle)$$

Where x and y are spatial coordinates, $S_i$ is the output of the first detector when core i is excited, $R_i$ is the output of the second detector 134 and $I_i(x,y)$ is the supermode image. Angle brackets indicate an ensemble average. $O_i(x,y)$ may be described as a ghost image output.

Figure 8:
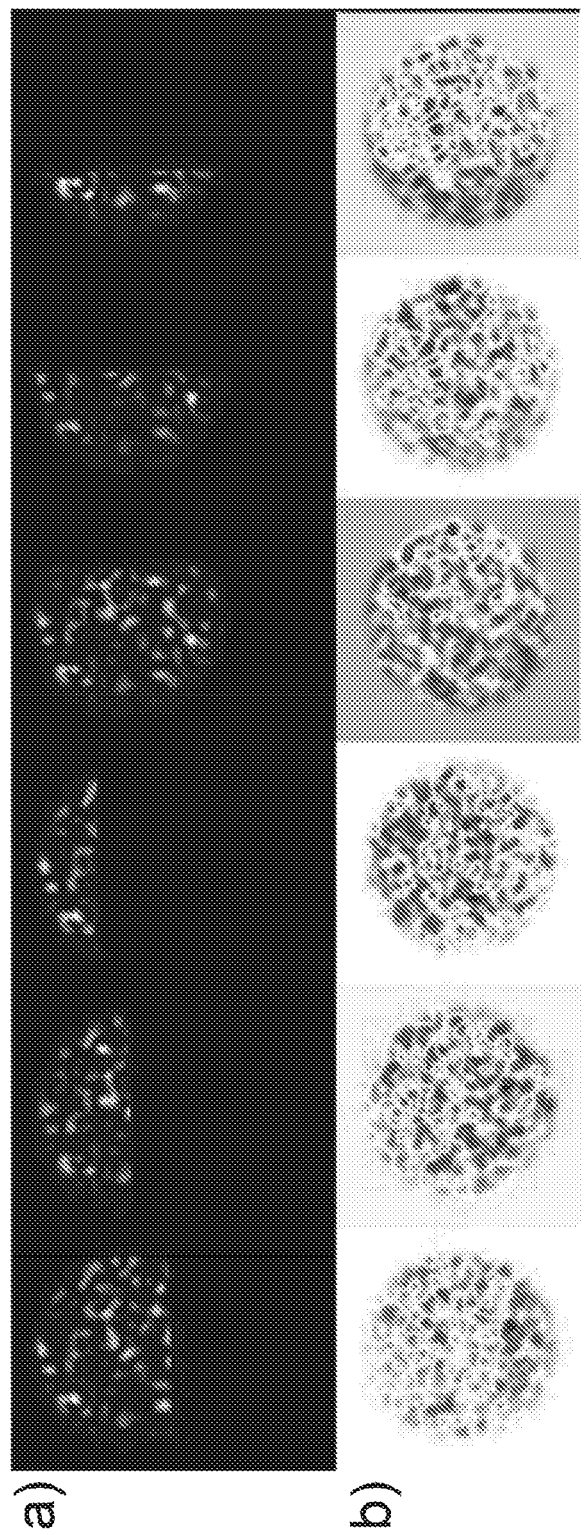
FIG. 8 shows a) a plurality of micrographs of an imaged object and b) ghost image outputs corresponding to the micrographs.
Figure 9:
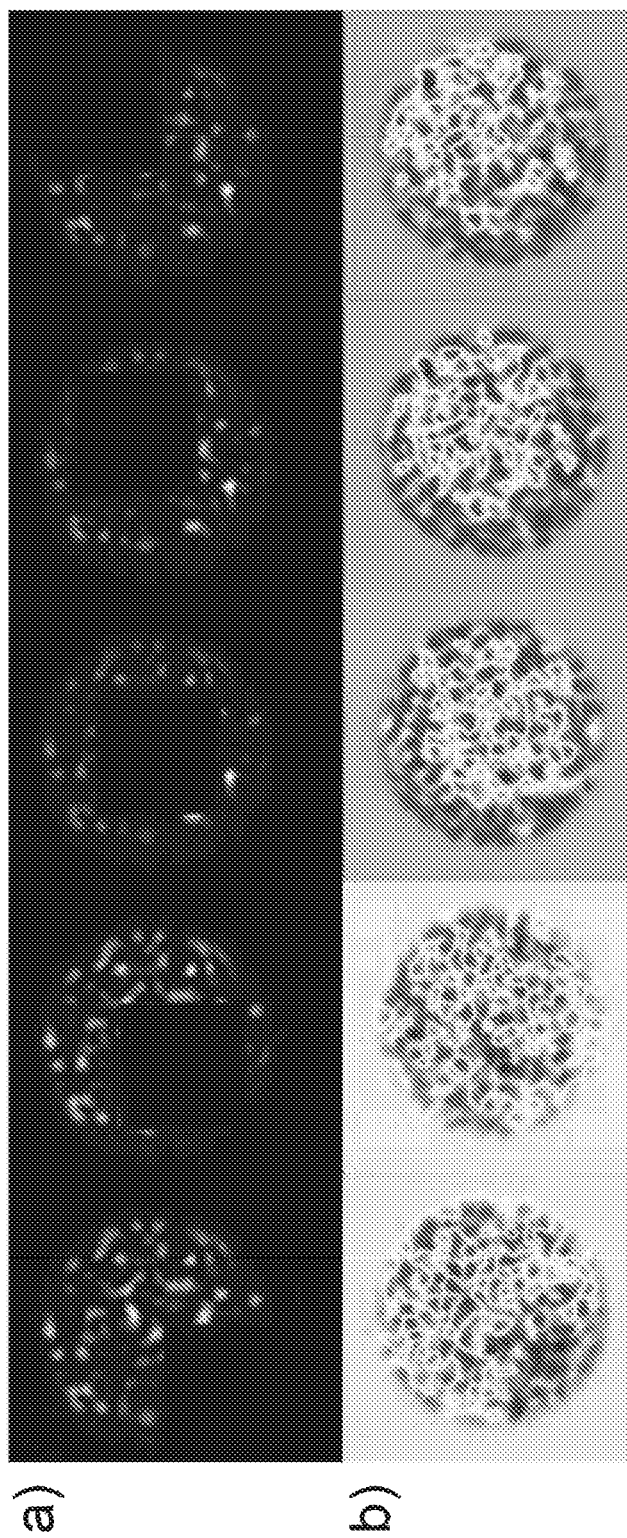

FIGS. 8 and 9 show results of the imaging process described above in relation to the apparatus of FIG. 7.

A first row of images, a), in FIG. 8 comprises a set of micrographs of an object in different positions. A second row of images, b), in FIG. 8 comprises a set of ghost images for object positions corresponding to those of the micrographs of the first row of images.

A first row of images, a), in FIG. 9 comprises a set of micrographs of a further, square object in different positions. A second row of images, b), in FIG. 9 comprises a set of ghost images for positions of the further object corresponding to those of the micrographs of the first row of images in FIG. 9.

Although embodiments using optical fibres are described above, in other embodiments any waveguides may be used. In one embodiment, the waveguide transition is scribed into a chip. The waveguide transition couples a plurality of single mode or few mode waveguides into a multimode waveguide.

Methods used above may be used for waveguides guiding any suitable frequencies, for example guiding light having a wavelength between 200 nm and 15 µm.

In embodiments above, an optical fibre apparatus is used to perform endoscopic imaging. Any other embodiments, any suitable waveguide apparatus may be used to perform any appropriate type of imaging, for example depth tomography or TIRF. In further embodiments, a waveguide apparatus may be used as described above to obtain information from multiple light patterns, where the information may not comprise an image.

Embodiments of the waveguide apparatus may be used to perform imaging or analysis of any suitable anatomical region, for example any anatomical region that is capable of being accessed via an endoscope. For example, embodiments may be used to perform imaging of the bronchus, gastrointestinal tract, urinary tract, or brain. Imaging may be performed on any suitable human or animal subject. Imaging may be performed for any suitable medical or veterinary application.

Features of embodiments above may be combined with features of other embodiments. For example, phase control may be used in conjunction with beat frequencies.

It may be understood that the present invention has been described above purely by way of example, and that modifications of detail can be made within the scope of the invention.

Each feature disclosed in the description and (where appropriate) the claims and drawings may be provided independently or in any appropriate combination.

The invention claimed is:

1. A system comprising:
a waveguide apparatus comprising a plurality of input waveguides, a multimode waveguide, and a guided-wave transition coupling the plurality of input waveguides to the multimode waveguide, wherein a length of the multimode waveguide is much shorter than a length of the waveguide apparatus, wherein each of the input waveguides is a single mode waveguide, and wherein each of the input waveguides is polarization maintaining;
at least one light source configured to excite in turn each of a plurality of the input waveguides, or each of a plurality of combinations of the input waveguides, or individually each of the input waveguides, thereby generating a plurality of different light patterns in turn at an output of the waveguide apparatus,
wherein the waveguide apparatus is configured to direct each of the plurality of different light patterns to a target region; and
at least one detector configured to detect light transmitted, reflected or emitted from the target region in response to each of the different light patterns, and to output signals representing the detected light,
wherein each of the plurality of different light patterns formed when a single core of a multi-core section of the waveguide apparatus is excited is insensitive to bending of the waveguide apparatus.

2. The system according to claim 1, further comprising a resource configured to process the signals from the at least one detector to obtain an image of the target region.

3. The system according to claim 2, wherein at least one of:
a) the processing of the signals from the at least one detector to obtain the image of the target region comprises, for each of the different light patterns, combining an image of that light pattern with the signal obtained from the at least one detector for that light pattern; or
b) the processing of the signals from the at least one detector to obtain the image of the target region comprises ghost imaging.

4. The system according to claim 1, wherein the waveguide apparatus comprises an optical fibre apparatus; each of the input waveguides comprises a respective core of a multi-core section of the optical fibre apparatus; and wherein the multimode waveguide comprises a multimode section of the optical fibre apparatus.

5. The system according to claim 4, wherein at least one of:
a) the guided-wave transition comprises a substantially continuous transition from the cores of the multi-core section of the optical fibre apparatus to the multimode section of the optical fibre apparatus;
b) the guided-wave transition comprises a photonic lantern transition; or
c) the multi-core section and multimode section are formed from the same optical fibre.

6. The system according to claim 1, wherein the system comprises or forms part of an endoscopic imaging apparatus.

7. The system according to claim 1, wherein the at least one light source is configured to excite in turn individual modes of the input waveguides.

8. The system according to claim 1, configured such that light propagating in any one of the input waveguides is substantially not coupled to any other one of the input waveguides.

9. The system according to claim 1, further comprising a support configured to eliminate or reduce bending of the guided-wave transition in response to bending of the waveguide apparatus.

10. The system according to claim 1, wherein at least one of:
   a) each of the different light patterns formed when a single core of a multi-core section of the waveguide apparatus is excited is insensitive to bending of the waveguide apparatus;
   b) at least some of the different light patterns are substantially orthogonal to each other in an electromagnetic field; or
   c) the different light patterns are such that all of the target region is illuminated by the light patterns.

11. The system according to claim 1, wherein at least one of:
   a) the image comprises a total internal reflection fluorescence (TIRF) image; or
   b) the image comprises a depth tomography image.

12. The system according to claim 1, wherein the waveguide apparatus further comprises a further guided-wave transition.

13. The system according to claim 1, wherein the further guided-wave transition is controllably deformable.

14. The system according to claim 1, wherein the at least one light source is configured to excite each of the input waveguides with a plurality of different wavelengths, thereby producing a plurality of light patterns for each of the input waveguides.

15. The system according to claim 1, wherein the at least one light source is configured to excite in turn each of a plurality of combinations of the input waveguides, wherein exciting each combination comprises exciting at least some of the plurality of input waveguides simultaneously using at least one of selected amplitudes or selected phases to produce a desired light pattern at the output of the waveguide apparatus.

16. The system according to claim 15, wherein at least one of:
   a) the desired light pattern comprises a spot of light positioned at a distal surface of the waveguide apparatus;
   b) the desired light pattern comprises a spot of light positioned within the target region; or
   c) each of the different light patterns comprises a spot of light at a different respective position, such as to scan the spot of light across the target region.

17. The system according to claim 15, wherein at least one of:
   a) the system is further configured to perform a calibration process to obtain calibration data, wherein the at least one of the selected amplitudes or the selected phases are based on the calibration data;
   b) the system further comprises a partially reflecting element configured to partially reflect the light patterns, and a detector configured to receive the reflected part of the light patterns and to output signals representing the reflected part of the light patterns; or
   c) the processor is configured to determine the at least one of the selected amplitudes or the selected phases are based on the signals representing the reflected part of the light patterns.

18. The system according to claim 1, wherein exciting in turn each of a plurality of combinations of the input waveguides comprises exciting in turn each of a plurality of pairs of input waveguides, the exciting of each of the pairs comprising exciting a first input waveguide of the pair with light of a first frequency, and exciting a second input waveguide of the pair with light of a second frequency.

19. The system according to claim 18, wherein at least one of:
   a) the resource is configured to process the signals from the at least one detector to obtain for each pair of the plurality of pairs of waveguides at least one beat frequency; or
   b) the input waveguides are excited with a plurality of different frequencies, thereby obtaining a plurality of different beat frequencies.

20. The system according to claim 1, wherein exciting each combination of the input waveguides comprises exciting a respective first one of the input waveguides with a first frequency of light and exciting a respective second one of the input waveguides with a second frequency of light, and wherein the system further comprises a processor configured to process the signals from the at least one detector to obtain a beat frequency for each of the combinations.

21. The system according to claim 1, wherein a length of the multimode waveguide and the guided-wave transition is much shorter than a length of the waveguide apparatus.

22. The system according to claim 1, wherein the waveguide apparatus is an endoscopic waveguide apparatus, and wherein the target region is at a distal end of the waveguide apparatus and the detector is configured to detect light reflected or emitted from the target region and transmitted to a proximal end of the waveguide apparatus.

23. A system comprising:
   a waveguide apparatus comprising a plurality of input waveguides, a multimode waveguide, and a guided-wave transition coupling the plurality of input waveguides to the multimode waveguide, wherein a length of the multimode waveguide is much shorter than a length of the waveguide apparatus, wherein each of the input waveguides is a single mode waveguide, and wherein each of the input waveguides is polarization maintaining;
   at least one light source configured to excite the input waveguides with a plurality of different sets of at least one of selected amplitudes or selected phases in turn, thereby generating a plurality of different desired light patterns in turn at an output of the waveguide apparatus,
   wherein the waveguide apparatus is configured to direct each of the plurality of different desired light patterns to a target region; and
   at least one detector configured to detect light transmitted, reflected or emitted from the target region in response to each of the different desired light patterns, and to output signals representing the detected light,
   wherein each of the plurality of different desired light patterns formed when a single core of a multi-core section of the waveguide apparatus is excited is insensitive to bending of the waveguide apparatus.

24. A method comprising:

by at least one light source, exciting in turn each of a plurality of input waveguides of a waveguide apparatus, or a plurality of combinations of the input waveguides, or individually each of the input waveguides, or exciting the input waveguides with a plurality of different sets of at least one of selected amplitudes or selected phases in turn, thereby generating a plurality of different light patterns in turn at an output of the waveguide apparatus, wherein each of the plurality of different light patterns formed when a single core of a multi-core section of the waveguide apparatus is excited is insensitive to bending of the waveguide apparatus, wherein the waveguide apparatus comprises the plurality of input waveguides, a multimode waveguide, and a guided-wave transition coupling the plurality of input waveguides to the multimode waveguide, wherein a length of the multimode waveguide is much shorter than a length of the waveguide apparatus, and wherein each of the input waveguides is a single mode waveguide, and wherein each of the input waveguides is polarization maintaining;

directing by the waveguide apparatus each of the plurality of different light patterns to a target region;

detecting by at least one detector light transmitted, reflected or emitted from the target region in response to each of the different light patterns; and outputting by the detector signals representing the detected light.

* * * * *